(12) United States Patent
Panotopoulos

(10) Patent No.: US 8,398,581 B2
(45) Date of Patent: Mar. 19, 2013

(54) FLUID EXCHANGE CATHETER SYSTEM

(75) Inventor: Christos Panotopoulos, Athens (GR)

(73) Assignee: Irras AB, Stockholm (SE)

( * ) Notice: Subject to any disclaimer, the term of this patent is extended or adjusted under 35 U.S.C. 154(b) by 413 days.

(21) Appl. No.: 12/065,019

(22) PCT Filed: Aug. 25, 2006

(86) PCT No.: PCT/GR2006/000043
§ 371 (c)(1),
(2), (4) Date: Feb. 27, 2008

(87) PCT Pub. No.: WO2007/026182
PCT Pub. Date: Mar. 8, 2007

(65) Prior Publication Data
US 2008/0200877 A1 Aug. 21, 2008

(30) Foreign Application Priority Data
Sep. 2, 2005 (GR) ............... 20050100452

(51) Int. Cl.
A61M 3/00 (2006.01)
A61M 1/00 (2006.01)
A61M 5/00 (2006.01)
A61M 5/32 (2006.01)

(52) U.S. Cl. ........... 604/43; 604/120; 604/173; 604/266

(58) Field of Classification Search ............. 604/43–45, 604/94.01, 118–121, 173, 258, 264, 266–269, 604/284, 103.01
See application file for complete search history.

(56) References Cited

U.S. PATENT DOCUMENTS

| | | | |
|---|---|---|---|
| 2,560,915 A * | 7/1951 | Bamberger | ............ 604/45 |
| 3,669,116 A | 6/1972 | Heyer | |
| 3,955,574 A | 5/1976 | Rubinstein | |
| 4,228,802 A | 10/1980 | Trott | |
| 4,694,832 A | 9/1987 | Ungerstedt | |
| 4,755,175 A | 7/1988 | Nilsson | |

FOREIGN PATENT DOCUMENTS

| | | |
|---|---|---|
| EP | 0251512 A1 | 1/1988 |
| GB | 1451418 A | 10/1976 |
| WO | WO 03/089031 A1 | 10/2003 |
| WO | WO 2005/023354 | 3/2005 |

* cited by examiner

Primary Examiner — Nicholas Lucchesi
Assistant Examiner — Nathan R Price
(74) Attorney, Agent, or Firm — The Webb Law Firm

(57) ABSTRACT

A catheter system that can be used for concurrent fluid infusion and aspiration in humans, animals and biological material, at a wide range of flow rates, without any blockage problems. The system has devices that control the infused liquid's pressure changes accordingly to the aspirated liquid's pressure changes, in order to allow accurate and safe fluid exchange flow control and create changes of pressures at the catheter's tip that do not allow the catheter's blockage.

22 Claims, 2 Drawing Sheets

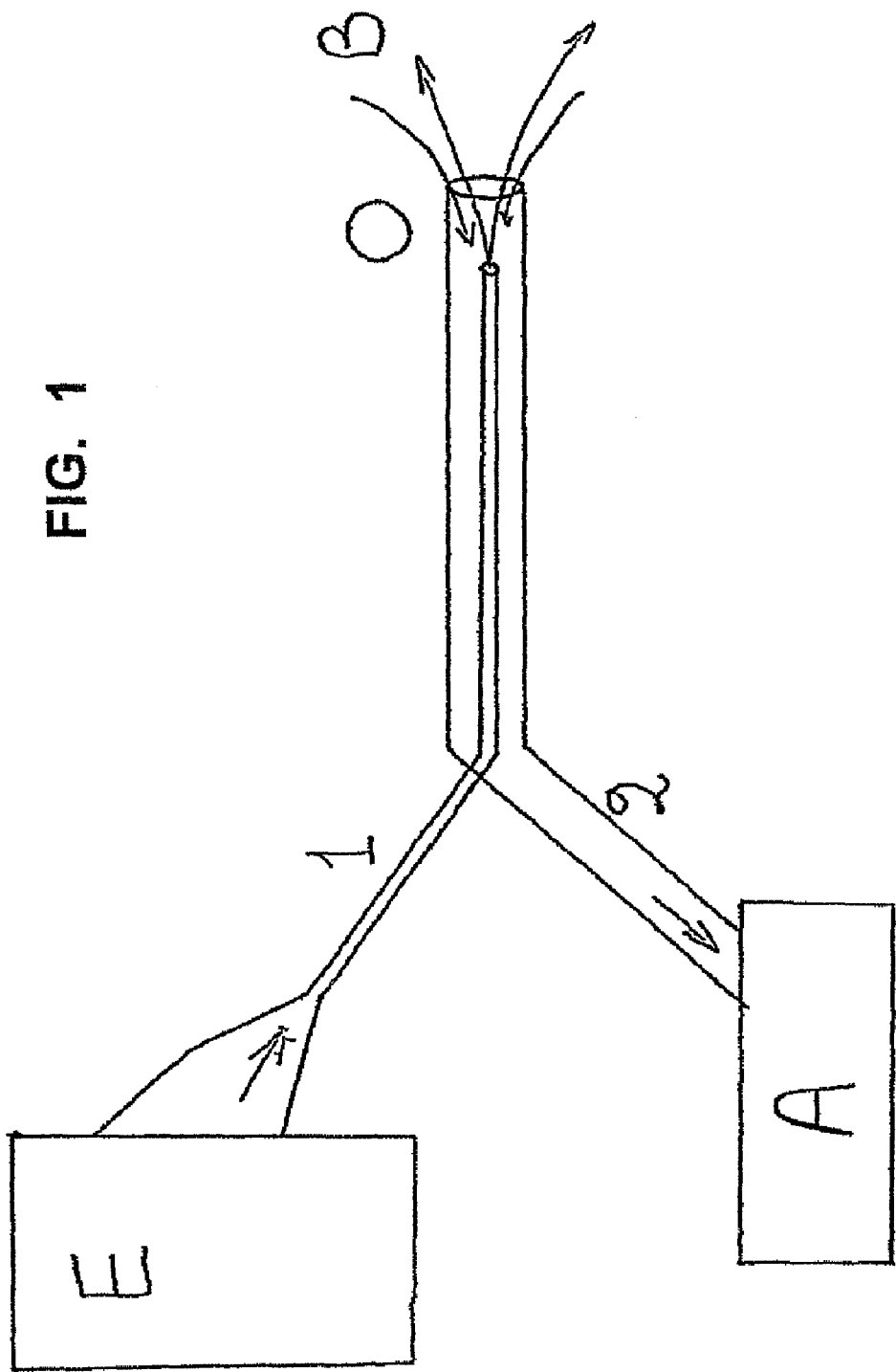

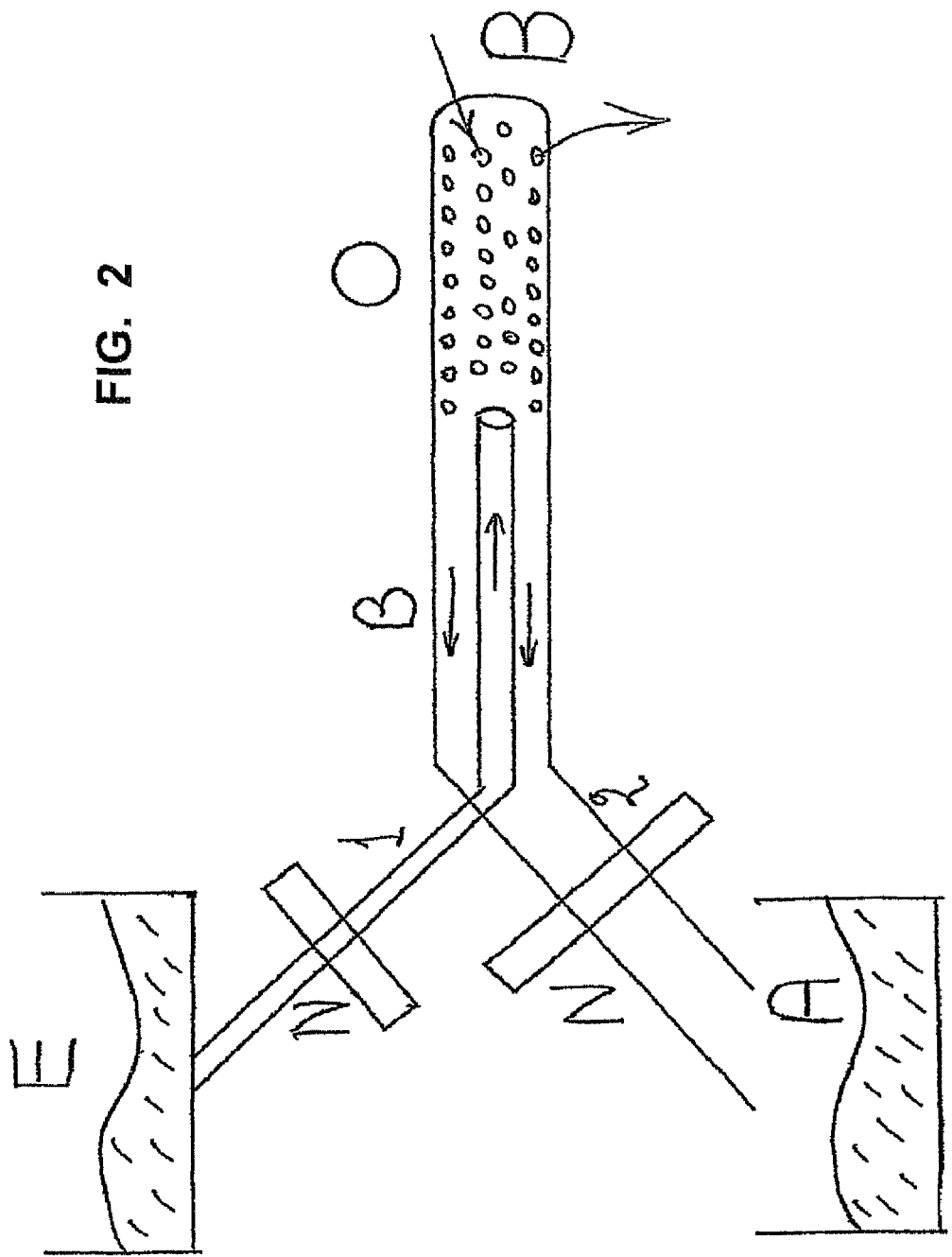

FLUID EXCHANGE CATHETER SYSTEM

BACKGROUND OF THE INVENTION

1. Field of the Invention

The present invention relates to a catheter's system that can be used for infusion of fluids (drugs, water and nutrients) to the body, with concurrent aspiration of biological material (blood, pus, pathological tissue, toxic substances) from the body, in human and, or, animal tissue, without any blockage problems.

2. Description of the Related Art

There are many kinds of catheters which are used for fluid infusion and aspiration in a clinical or preclinical setting. Traditionally, the catheter's tip that is inserted in biological material, is called "distal" and the tip that stays outside is called "proximal".

Most of existing catheters have a single lumen and through this lumen the user can alternatively infuse or aspirate liquids.

For example, in a clinical setting, the common intravenous catheter either aspirates blood samples—usually immediately after it's insertion to the vein—or infuses solutions of drugs and, or, nutrients—usually for many hours or days following insertion.

These catheters can infuse or aspirate large quantities of liquids, but they cannot do it concurrently in order to have a constant exchange of drugs and nutrients with the extra-cellular fluid or pathological liquid accumulations of the tissue.

The concurrent fluid exchange is desirable both for monitoring and therapeutic reasons.

There are few catheters with multiple lumina, which can concurrently infuse and aspirate liquids.

For example, the microdialysis catheter after its introduction to a human or animal tissue, is continuously perfused with liquid solutions from a pump connected to its proximal tip. The catheter consists of two concentric lumina, or tubes, that are covered at their distal tip by a membrane. Usually the central tube is the efferent and the peripheral tube is the afferent part of the catheter. Part of the perfused liquid is infused to the tissue through the catheter's membrane at its distal end, and extra-cellular fluid is aspirated through the same membrane and the efferent lumen.

Microdialysis catheters and similar catheters, however, were designed for tissue monitoring, and the above described concurrent infusion and aspiration takes place at a few microliter/minute rate flow range and through very small membrane pores.

For therapeutic applications we need much greater liquid exchange rate and membranes or cages with big pores so that it is possible to evacuate low viscosity liquids like pus, that block all existing catheters.

A common problem of all kinds of existing catheters for biological fluids, is their blockage, due to corking of biological material into their lumen's tip or it's covering.

For example, the endotherapy catheter system claims to possess the desired liquid exchange rate and blockage free operation through a moving part.

It consists of two concentrical tubes, one infusing and one aspirating, connected properly to infusion and aspiration devices at their proximal tip, and having a filter or membrane or grid or mesh cage covering their distal tip, which contains an hydrodynamically moving device for concurrent infusion and aspiration. The infusing tube is appropriately connected to a moving device that irrigates the surrounding the catheter space, while simultaneously propels with its movement the aspiration through the other tube.

The following documents are considered the most relevant state of the art as mentioned above:

D1: U.S. Pat. No. 4,694,832 (UNGERSTEDT CARL U) 22 Sep. 1987
D2: U.S. Pat. No. 4,755,175A (NILSSON LEIF) 5 Jul. 1988
D3: PCT/GR2004/000045, IPC A61M 25/00, (PANOTOPOULOS CHRISTOS), 8 Sep. 2003.

SUMMARY OF THE INVENTION

According to the present invention, provided is a fluid exchange catheter system, including infusion and aspiration devices connected to a catheter having two or more lumina. The system further includes a mechanism for creating programmable changes of pressure in infusing and aspirating lumen of the catheter. Accordingly, infused fluids mix with biological fluids, and the mechanism allows this fluid mixture to evacuate without catheter blockage.

BRIEF DESCRIPTION OF THE DRAWINGS

FIG. 1 is a schematic view of one embodiment of a fluid exchange catheter system according to the present invention; and FIG. 2 is a schematic view of another embodiment of a fluid exchange catheter system according to the present invention.

DETAILED DESCRIPTION OF THE PREFERRED EMBODIMENTS

As illustrated in schematic form in FIGS. 1 and 2, provided is a fluid exchange catheter system consists of two or more lumina, or tubes, (1,2), connected properly to infusion (E) and aspiration (A) devices at their proximal tips, and having a filter or membrane or grid or mesh cage or no covering over their distal tips (O). These infusion and aspiration devices periodically and, or, continuously change liquid pressure gradients in the system (nevertheless assuring a flow rate that meets the needs for infusion and aspiration of the underlying pathology, or the monitoring, or therapeutic, or research protocol's, needs), in order to create fluid currents (B) that wash clean the catheter's tip and keep unobstructed the fluid exchange between the catheter and the tissue, without the need of any moving parts.

The pressure differences in the system are created by any pattern of positive pressures of the infusing pump and the accordingly synchronized pattern of negative pressures of the aspirating pump (pressures always refer to the pressure at the catheter's tip surrounding tissue).

The system allows a fully and safely controllable infusion-aspiration rate and unobstructed fluid exchange.

For example, in one of the many possible system's versions regarding construction and operational mode, a peristaltic pump (E) is programmed to infuse the liquid with a +200 mmHg pressure for 5 sec followed by 10 sec of stop, while the aspirating tube is blocked (N), and a peristaltic pump (A) is programmed to aspirate with a −100 mmHg pressure during the next 15 sec, while the infusing tube is blocked (N), in a 30 sec cycle of operation.

Lots of patterns of pressure changes can be applied depending on the underlying pathology or the research protocol. Both these (infusion and aspiration) pressures at the ends of the system, can be monitored to be kept synchronized into a predetermined range and phase difference and can be protected by alarms and automatic stops (N), whenever there is any system's dysfunction detection, by flow and, or, pressure detector devices (N) placed appropriately in the system for safety (against over-infusion, over-aspiration etc).

Alternatively the infusion and aspiration devices of the system can be fluid containers (E, A), simply using the hydrostatic pressure forces created by their position relative to the catheter's tip, as moving forces for the infused fluid to enter and the aspirated fluid to leave the tissue at the catheter's insertion site.

For this version of the fluid exchange catheter's system, we could simply include only one automatic button (N) programmed to compress the aspirating (and infusing) tube for 5 sec, followed by 5 sec of free flow of the aspirated (and infused) fluid or programmed for any other pattern of time intervals for free and blocked flow.

Any mode of synchronized changes of pressure at any point of the fluid exchange catheter's system, is transferred directly at the infusing and aspirating tip of the catheter through the liquid column of infused or aspirated fluids.

FIGS. 1 and 2 represent some of the many possible variations of the fluid exchange catheter's system.

The fluid exchange catheter has a bifurcation part of any configuration, in order to split the two opposite flows in two different lumina.

The distal end of the outer lumen, or tube, holds an exchange surface, that can be a filter or membrane or grid or mesh cage or nothing—just the open tip of the aspirating lumen.

Fluid, which can vary from distilled water to nutrient solutions with drugs, that is supplied through the infusion device (E) to the inner lumen, or tube, (1), reaches the distal end of the catheter (O), where substance exchange occurs between the infused fluid and substances contained in the surrounding tissue's extracellular fluid. The fluid mixture returns to an aspiration device or collection tank (A). Arrows represent pressure gradients.

In order to remove organic substances that are built up on the exchange surface, and consequently block the catheter, a fluid jet, receiving its supply from the inner lumen's hole(s), is dispersed against the liquid exchange surface's inner wall periodically, unblocking thus the membrane or mesh or grid or filter covering. When just the open tip of the aspirating lumen is the exchange surface, the jet from the infusing lumen unblocks the aspirating lumen.

The construction material of the catheter's system should be in conformity to the norms and regulations existing for clinical and laboratory catheters, including biocompatibility issues etc.

The invention claimed is:

1. A fluid exchange catheter system, comprising:
   an inner lumen having a proximal end and a distal end, wherein the proximal end of the inner lumen is connected to an infusion fluid source;
   an infusion mechanism operably connected with the inner lumen to pass infusion fluid from the infusion fluid source through the inner lumen to discharge at an opening in the distal end of the inner lumen;
   an outer lumen having a proximal end, a distal end and a lumen wall extending between the proximal end and the distal end forming an interior lumen space, wherein the outer lumen is operably connected to an aspiration mechanism;
   wherein the infusion mechanism and the aspiration mechanism are programmed to create a pattern of positive pressure in the inner lumen and a synchronized pattern of negative pressure in the outer lumen; and
   wherein the distal end of the inner lumen is disposed within the interior lumen space of the outer lumen such that a fluid exiting the inner lumen through an opening in the distal end of the inner lumen flows into the interior lumen space of the outer lumen.

2. The fluid exchange catheter system of claim 1, further comprising an exchange surface disposed at the distal end of at least one of the inner lumen and the outer lumen.

3. The fluid exchange catheter system of claim 2, wherein the exchange surface is selected from the group consisting of a filter, a membrane, a grid, and a mesh cage.

4. The fluid exchange catheter system of claim 2, wherein the exchange surface is disposed at the distal end of the outer lumen.

5. The fluid exchange catheter system of claim 3, wherein the exchange surface is disposed at the distal end of the outer lumen.

6. The fluid exchange catheter system of claim 1, wherein at least one of the infusion mechanism and the aspiration mechanism is a peristaltic pump.

7. The fluid exchange catheter system of claim 1, wherein at least one of the infusion mechanism and the aspiration mechanism is a fluid container.

8. The fluid exchange catheter system of claim 1, wherein the distal end of the outer lumen forms a catheter tip, and
   wherein the pattern of positive pressure in the inner lumen and the synchronized pattern of negative pressure in the outer lumen create fluid currents at the catheter tip for keeping the catheter tip unobstructed.

9. The fluid exchange catheter system of claim 8, wherein the catheter tip comprises an exchange surface.

10. The fluid exchange catheter system of claim 9, wherein the exchange surface is selected from the group consisting of a filter, a membrane, a grid, and a mesh cage.

11. The fluid exchange catheter system of claim 1 wherein the distal end of the outer lumen comprises at least one opening and the opening in the distal end of the inner lumen is disposed at a proximal position relative to the at least one opening in the distal end of the outer lumen.

12. The fluid exchange catheter system of claim 1, wherein the infusion mechanism creates changes of positive pressure in the inner lumen to control the infusion rate and the aspiration mechanism creates changes of negative pressure in the outer lumen to control the aspiration rate.

13. The fluid exchange catheter system of claim 12, wherein the distal end of the outer lumen forms a catheter tip, and
   wherein the pattern of positive pressure in the inner lumen and the synchronized pattern of negative pressure in the outer lumen create fluid currents at the catheter tip for keeping the catheter tip unobstructed.

14. A fluid exchange catheter system, comprising
   a catheter;
   an inner lumen included in said catheter and having a distal end and a proximal end, said proximal end connected to an infusion fluid source;
   an infusion device operably connected with the inner lumen to pass infusion fluid from the infusion fluid source through the inner lumen to discharge at an opening in the distal end of the inner lumen;
   an outer lumen included in said catheter and having a distal end and a proximal end, said outer lumen operably connected to an aspiration device, and said distal end comprising a liquid exchange surface; and
   a mechanism programmed to create a pattern of positive pressure in said inner lumen and a synchronized pattern of negative pressure in said outer lumen, and to disperse a fluid jet exiting said inner lumen against said liquid exchange surface in order to remove organic substance built up on said liquid exchange surface and to allow infused fluids to mix with biological fluids and to evacuate this fluid mixture without catheter blockage.

15. The system of claim 14, wherein said mechanism is programmed to block said inner lumen for a first time interval followed by a second time interval of free flow of the fluid through said inner lumen.

16. The system of claim 14, wherein said mechanism is programmed to block said outer lumen for a first time interval followed by a second time interval of free flow of the fluid through said outer lumen.

17. The system of claim 14, wherein said exchange surface defines an open tip of said outer lumen.

18. The system of claim 14, wherein said exchange surface comprises a member selected from the group consisting of a filter, a membrane, a grid, and a mesh.

19. The system of claim 14, wherein said inner lumen is disposed essentially concentrically within said outer lumen.

20. The system of claim 14, wherein said inner and outer lumens are separate tubes at their distal ends.

21. The system of claim 14, wherein said mechanism is programmed to:
 infuse liquid through said inner lumen with a first pressure for a first time interval followed by a second time interval of stop, wherein said outer lumen is blocked during said first and second time intervals, and
 aspirate fluid through said outer lumen with a second pressure being lower than said first pressure during a third time interval, wherein said inner lumen is blocked during said third time interval.

22. The system of claim 14, wherein the mechanism creates changes of positive pressure in said inner lumen to control infusion rate and changes of negative pressure in said outer lumen to control aspiration rate.

* * * * *